United States Patent
Ke et al.

(10) Patent No.: US 12,396,638 B2
(45) Date of Patent: Aug. 26, 2025

(54) SYSTEMS AND METHODS FOR DRY EYE ANALYSIS USING TERAHERTZ RADIATION

(71) Applicants: AGENCY FOR SCIENCE, TECHNOLOGY AND RESEARCH, Singapore (SG); Singapore Health Services PTE LTD, Singapore (SG)

(72) Inventors: Lin Ke, Singapore (SG); Hongwei Liu, Singapore (SG); Nan Zhang, Singapore (SG); Jod S Mehta, Singapore (SG); Yu Chi Liu, Singapore (SG)

(73) Assignees: AGENCY FOR SCIENCE, TECHNOLOGY AND RESEARCH, Singapore (SG); SINGAPORE HEALTH SERVICES PTE LTD, Singapore (SG)

( * ) Notice: Subject to any disclaimer, the term of this patent is extended or adjusted under 35 U.S.C. 154(b) by 975 days.

(21) Appl. No.: 17/260,217

(22) PCT Filed: Jul. 10, 2019

(86) PCT No.: PCT/SG2019/050338
§ 371 (c)(1),
(2) Date: Jan. 13, 2021

(87) PCT Pub. No.: WO2020/013763
PCT Pub. Date: Jan. 16, 2020

(65) Prior Publication Data
US 2021/0259540 A1    Aug. 26, 2021

(30) Foreign Application Priority Data

Jul. 13, 2018   (SG) .......................... 10201806041W

(51) Int. Cl.
*A61B 3/107*    (2006.01)
*A61B 3/10*     (2006.01)
(Continued)

(52) U.S. Cl.
CPC ............ *A61B 3/101* (2013.01); *A61B 3/1005* (2013.01); *A61B 5/0507* (2013.01);
(Continued)

(58) Field of Classification Search
CPC ........ A61B 2560/0223; A61B 2576/02; A61B 3/1005; A61B 3/101; A61B 5/0507; A61B 5/14546; A61B 5/4875
See application file for complete search history.

(56) References Cited

U.S. PATENT DOCUMENTS

2009/0318815 A1 * 12/2009 Barnes .................. A61B 5/444
                                                                382/128
2013/0162949 A1    6/2013 Culjat et al.
(Continued)

FOREIGN PATENT DOCUMENTS

| CN | 104422702 A | 3/2015 |
|---|---|---|
| FI | 127458 B | 6/2018 |
| WO | 2017181201 A1 | 10/2017 |

OTHER PUBLICATIONS

Bennett et al., "Assessment of corneal hydration sensing in the terahertz band: in vivo results at 100 GHz," Journal of Biomedical Optics, Sep. 30, 2012, vol. 17, No. 9, pp. 097008-1 to 0978008-7.
(Continued)

*Primary Examiner* — Christopher L Cook
(74) *Attorney, Agent, or Firm* — Womble Bond Dickinson (US) LLP

(57) ABSTRACT

Methods and systems for dry eye analysis using terahertz (THz) radiation. The method includes projecting a THz wave onto a surface of an eye and detecting a reflected wave being a reflection of the THz wave reflected from the surface of the eye. The method further includes analysing properties of the eye in response to the THz wave reflected from the surface of the eye, the properties of the eye including thickness of the eye's cornea and ambient tissues, and
(Continued)

analyzing the properties of the eye comprises measuring the thickness of the cornea and/or the ambient tissues and/or measuring an amount of chemical components of one or more of the eye's layers.

18 Claims, 10 Drawing Sheets

(51) Int. Cl.
  *A61B 5/0507* (2021.01)
  *A61B 5/00* (2006.01)
  *A61B 5/145* (2006.01)

(52) U.S. Cl.
  CPC ......... *A61B 5/14546* (2013.01); *A61B 5/4875* (2013.01); *A61B 2560/0223* (2013.01); *A61B 2576/02* (2013.01)

(56) References Cited

U.S. PATENT DOCUMENTS

| | | | | |
|---|---|---|---|---|
| 2014/0240674 | A1* | 8/2014 | Wei | A61B 3/102 |
| | | | | 351/208 |
| 2016/0095533 | A1 | 4/2016 | Shang | |
| 2017/0370834 | A1* | 12/2017 | Kassab | G01J 3/10 |
| 2018/0325431 | A1* | 11/2018 | Guarin | A61B 5/0507 |
| 2019/0117109 | A1* | 4/2019 | Grundfest | A61B 5/4875 |

OTHER PUBLICATIONS

Sung, S. et al., "Direct measurement of corneal tissue water content by reflection imaging at Terahertz Frequencies," Investigative Ophthalmology & Visual Science, Jun. 2015, vol. 56, No. 7, 1644, 2 pages.

Behrens, A. et al., Dysfunctional Tear Syndrome: A Delphi Approach to Treatment Recommendations, Cornea Sep. 2006, vol. 25, Issue 8, 2 pages.

International Preliminary Report on Patentability for PCT International Application No. PCT/SG2019/050338, issued Jan. 19, 2021, 6 pages.

International Search Report for PCT International Application No. PCT/SG2019/050338, mailed Sep. 2, 2019, 4 pages.

Lemp, M. et al., "The Definition & Classification of Dry Eye Disease," Guidelines from the 2007 International Dry Eye Workshop, Apr. 2008, 6 pages.

Written Opinion for Singapore Patent Application No. 11202100382Q, dated Oct. 20, 2023, 8 pages.

Written Opinion of the International Searching Authority for Singapore International Application No. PCT/SG2019/050338, mailed Sep. 2, 2019, 5 pages.

\* cited by examiner

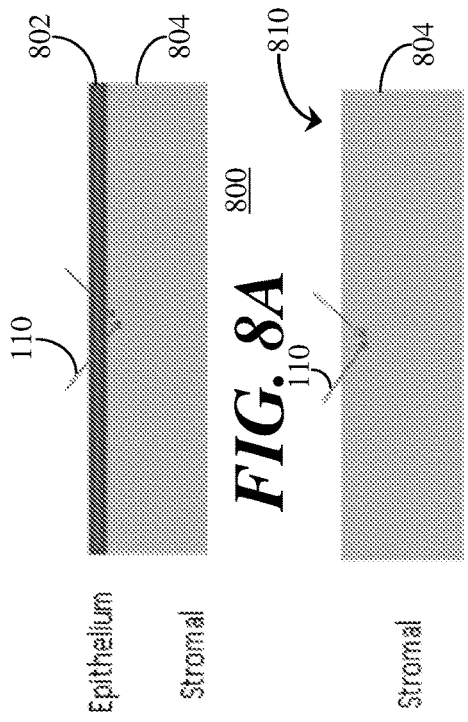
FIG. 8A
FIG. 8B
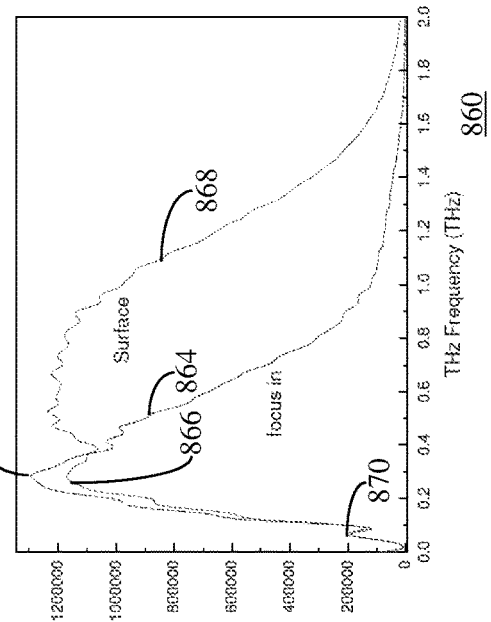
FIG. 8D
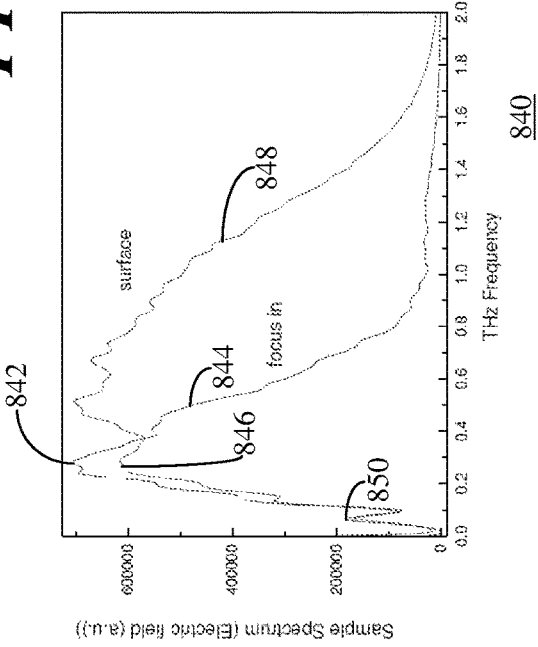
FIG. 8C

SYSTEMS AND METHODS FOR DRY EYE ANALYSIS USING TERAHERTZ RADIATION

CROSS-REFERENCE TO RELATED APPLICATIONS

This patent application is a U.S. National Phase Application Under 35 U.S.C. § 371 of International Application No. PCT/SG2019/050338, filed 10 Jul. 2019, entitled "SYSTEMS AND METHODS FOR DRY EYE ANALYSIS USING TERAHERTZ RADIATION," which claims the benefit of priority of Singapore Patent Application No. 10201806041W, filed on 13 Jul. 2018.

TECHNICAL FIELD

The present invention generally relates to dry eye analysis, and more particularly relates to systems and methods for dry eye analysis using terahertz (THz) time-domain spectroscopy.

BACKGROUND OF THE DISCLOSURE

The term "dry eye" includes a wide spectrum of alterations of the ocular surface with different etiology and pathophysiology. As a consequence, even the definition of dry eye is still debated, as demonstrated by the fact that in 2006 it was recommended to use the designation of "dysfunctional tear syndrome" (DTS) instead of dry eye. The International Dry Eye Workshop (DEWS) considered dry eye as an ocular surface disease, which term includes both aqueous deficient and evaporative dry eye, lid related diseases (such as meibomian gland dysfunction (MGD) and anterior blepharitis), allergic conjunctivitis and other inflammatory, infective or iatrogenic conditions.

Currently available methods for diagnosis of dry eye include Schirmer's test, break-up time and ocular surface staining. Recent innovative noninvasive procedures include tear meniscus height measurement, corneal topography, functional visual acuity, tear interferometry, tear evaporimetry and tear osmolarity assessment.

Dry eye analysis can be considered as cornea and ambient tissue physical property changes. Corneal dystrophies, aging and diseases, however, can complicate dry eye analysis as the physical property changes due to disease or aging may relate to the cornea as well as the ambient tissues' components' (e.g., hydration, collagen and keratocytes) changes or corneal component non-uniformity changes.

Conventional methods and systems for monitoring chemical components changes in cornea as well as ambient tissues still focus on monitoring the surface of cornea as well as ambient tissues. However, to fully characterize a subject's dry eye mechanism, it is crucial and significant that the overall eye evaluation necessarily include corneal as well as ambient tissue layer thickness changes and chemical components changes resolved into individual layers.

Thus, what is needed are systems and methods for dry eye analysis which evaluates corneal and ambient tissue layer thickness changes and chemical components changes within individual layers of a subject's eye with enhanced sensitivity and selectivity. Furthermore, other desirable features and characteristics will become apparent from the subsequent detailed description and the appended claims, taken in conjunction with the accompanying drawings and this background of the disclosure.

SUMMARY

According to at least one embodiment of the present invention, a system for dry eye analysis using terahertz (THz) radiation is provided. The system includes a terahertz radiation measuring system and a signal processing unit. The terahertz radiation measuring system includes a terahertz radiation generator configured to project a THz wave onto a surface of an eye and a terahertz radiation detector configured to detect a reflected THz wave reflected from the surface of the eye. The signal processing unit is configured to communicate with the terahertz radiation detector to analyse properties of the eye in response to the THz wave reflected from the surface of the eye. The properties of the eye include thickness of the eye's cornea and ambient tissues and the signal processing unit analyzing the properties of the eye includes measuring the thickness of the cornea and/or the ambient tissues and/or measuring an amount of chemical components of one or more of the eye's layers.

According to another embodiment of the present invention, a method for dry eye analysis using THz radiation is provided. The method includes projecting a THz wave onto a surface of an eye and detecting a reflected wave being a reflection of the THz wave reflected from the surface of the eye. The method further includes analysing properties of the eye in response to the THz wave reflected from the surface of the eye, the properties of the eye including thickness of the eye's cornea and ambient tissues, and analyzing the properties of the eye comprises measuring the thickness of the cornea and/or the ambient tissues and/or measuring an amount of chemical components of one or more of the eye's layers.

According to a further embodiment of the present invention a computer readable medium comprising instructions which, when executed by a system, make the system perform a method for dry eye analysis using THz radiation is provided. The instructions include instructions to make the system project a THz wave onto a surface of an eye and detect a reflected THz wave reflected from the surface of the eye. The instructions further include instructions to make the system analyse properties of the eye in response to the THz wave reflected from the surface of the eye, the properties of the eye comprising thickness of the eye's cornea and ambient tissues, wherein analyzing the properties of the eye includes measuring the thickness of the cornea and/or the ambient tissues and/or measuring an amount of chemical components of one or more of the eye's layers.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with a present embodiment.

FIG. 8, comprising FIGS. 8A, 8B, 8C and 8D, depicts an illustration of how sublayer properties can be extracted non-invasively by focusing terahertz radiation through the epithelial layer and into the stroma layer of the eye, wherein FIG. 8A an illustration of focusing the terahertz radiation through the epithelial layer and into the stroma layer of the eye, FIG. 8B depicts an illustration of stripping of the epithelial layer and focusing the terahertz radiation through the stroma surface and into the stroma layer of the eye, FIG. 8C depicts a graph of results of the terahertz radiation focusing of FIG. 8A, and FIG. 8D depicts a graph of results of the terahertz radiation focusing of FIG. 8B.

FIG. 9, comprising FIGS. 9A and 9B, depicts graphs of properties of an epithelial layer of the eye as terahertz radiation is focused through the epithelial layer in accordance with the present embodiments using the system of FIG. 3, wherein FIG. 9A depicts a graph of time domain spectra as the terahertz radiation beam is focused from the epithelium surface down through the epithelium to the epithelium stroma interface, and FIG. 9B depicts a graph of frequency domain spectra as the terahertz radiation beam is focused from the epithelium surface down through the epithelium to the epithelium stroma interface.

FIG. 10, comprising FIGS. 10A and 10B, depicts graphs of frequency domain characteristics of the epithelial layer of the eye in accordance with the present embodiments as derived from the frequency domain spectra of FIG. 9B, wherein FIG. 10A depicts a graph of the frequency domain spectra of FIG. 9B when fast fourier transform (FFT) is performed on data only for the first peak in the time domain spectra of FIG. 9A, and FIG. 10B depicts a graph of the frequency domain spectra of FIG. 9B when fast fourier transform (FFT) is performed on data only for the second peak in the time domain spectra of FIG. 9A.

And FIG. 12, comprising FIGS. 12A and 12B, depicts graphs comparing time domain spectra results using terahertz radiation in accordance with the present embodiments of a set of five porcine eyes with ocular corneal thickness (OCT) measurements using conventional systems of the set of five porcine eyes, wherein FIG. 12A is a graph of the time domain spectra results using terahertz radiation in accordance with the present embodiments and FIG. 12 B is a graph of the OCT measurements using conventional systems.

Figure 1:
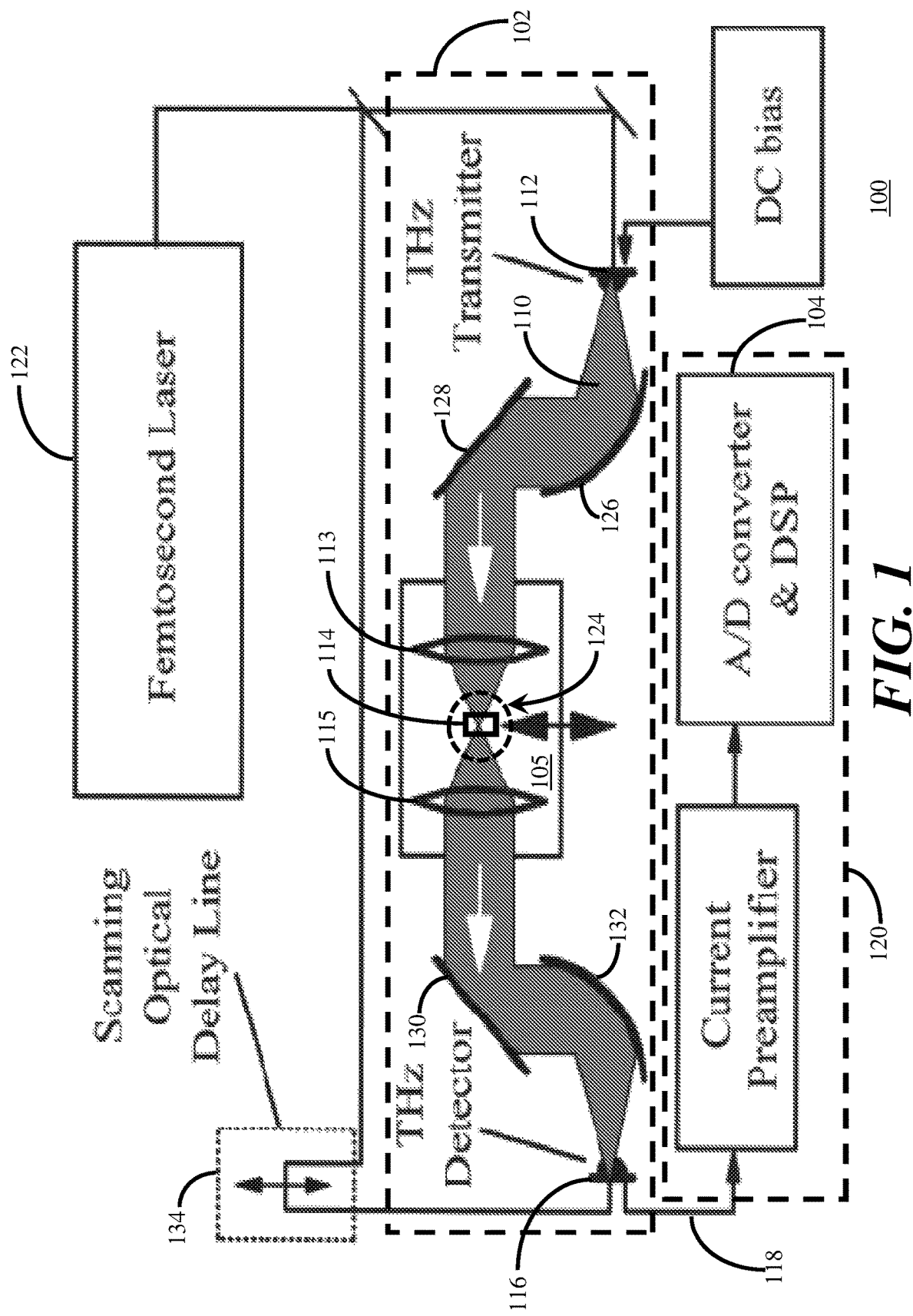
FIG. 1 depicts an illustration of a terahertz radiation measuring system in accordance with present embodiments.

Skilled artisans will appreciate that elements in the figures are illustrated for simplicity and clarity and have not necessarily been depicted to scale.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description. It is the intent of the present embodiment to present rapid, in vivo, non-invasive, non-destructive and non-contact systems and methods for dry eye tissue analysis which evaluate corneal and ambient tissue layer thickness changes and chemical components changes within individual layers of a subject's eye with enhanced sensitivity and selectivity.

According to the definition of dry eye adopted by the International Dry Eye Workshop (DEWS) in 2007, dry eye is "a multifactorial disease of the tears and ocular surface that results in symptoms of discomfort, visual disturbance and tear film instability with potential damage of the ocular surface. It is accompanied by increased osmolarity of the tear film and inflammation of the ocular surface."

Monitoring chemical component changes in the cornea as well as in ambient tissues is a method for analysis of the root reasons of dry eye formation. Therefore, dry eye analysis includes analysis of cornea and overall tissue physical property changes in layers of the eye. Corneal dystrophies, aging and diseases, however, can complicate dry eye analysis. The physical property changes due to disease or aging could very easily relate to corneal as well as ambient tissues' component changes such as hydration, collagen and keratocyte changes or to corneal component non-uniformity changes.

In accordance with present systems and methods, an accurate in-vivo instant terahertz measurement system is provided to extract in-vivo cornea as well as ambient tissues' component properties and chemical composition (such as hydration, collagen and keratocytes) and give information of the chemical component distribution vertically in order to analyse and monitor dry eye formation. While some conventional methods to evaluate dry eyes monitor changes of tear secretion or tear film then evaluate dry eye formation by evaluation of the tear film offline, the method in accordance with the present embodiments focuses on in vivo non-invasive and non-destructive analysis of the dry eye tissues.

Typical corneal thickness measurement is accomplished by optical coherence tomography, ultrasound, or interference of two light rays. For cornea as well as other eye ambient tissues' chemical component extraction (e.g., analysis of collagen, hydration and keratocytes composition), there are no reliable acknowledged methods.

Present embodiments address the drawbacks of prior art systems and methods by providing an in vivo non-invasive technology for measuring properties of the eye such as thickness of the eye's cornea and ambient tissues and/or measuring an amount of chemical components of one or more of the eye's layers. Embodiments of systems and methods of the present invention operate in the THz range in the electromagnetic spectrum which lies between microwave and infrared frequencies and generally defines frequencies ranging from 100 GHz ($10^{11}$ Hz, 3 mm wavelength) to 10 THz ($10^{13}$ Hz, 3.3 µm wavelength). Electromagnetic radiation in the THz range may also be referred to as THz light, THz radiation, or THz waveforms.

In accordance with present embodiments, a terahertz radiation measuring system, such as a terahertz portable system, analyses dry eye conditions in-vivo using terahertz time-domain spectroscopy. Referring to FIG. 1, an illustration 100 of a system for analysing dry eye conditions of an eye using terahertz (THz) radiation in accordance with present embodiments uses a THz time-domain (THz-TDS) system 102 to provide an illumination beam of terahertz radiation and a computer or other processing means 104.

The THz-TDS system 102 can be configured to reflect electromagnetic radiation 110 in THz range from a THz transmitter or emitter 112 toward a surface of an eye 114, receive THz light reflected from the eye at a THz detector or receiver 116, and generate a signal 118 indicative of the received radiation which is amplified and digitized by circuitry 120. The THz radiation is generated by the THz transmitter 112, such as an antenna or a nonlinear crystal, and pulsed in response to a signal from a femtosecond laser 122. The THz detector or receiver 116 can also be an antenna or a nonlinear crystal. The computer 104, which communicates with the THz-TDS system 102, can be configured to process the generated signal 118 and may further be configured for creating a visual imaging of the THz response from the surface or sublayers of the eye 114. A XYZ stage 105 can be configured to manipulate the structure of the THz-TDS system 102 to scan the surface of the eye 114 and move THz focal point 124 from a surface of the eye 114 to a level below the surface of the eye.

Thus, the system 100 for dry eye analysis includes an illumination system (e.g., the femtosecond laser 122 and the THz transmitter 112) configured to provide an illumination beam of terahertz radiation 110, an optical system including mirrors and lenses (e.g., lens 113) arranged in an optical path of the terahertz radiation 110 to relay and direct at least a portion of the illumination beam of terahertz radiation 110 onto an eye 114 of a subject and to receive at least a portion of terahertz radiation reflected from the eye to provide a return beam of terahertz radiation, and a detection system (e.g., detector 116) arranged in an optical path of said return beam of terahertz radiation, the detection system configured to provide a detection signal 118 from detecting at least a portion of said return beam of terahertz radiation. A signal processing system 120 is configured to communicate with the detection system 116 to receive the detection signal 118, wherein the signal processing system processes the detection signal to provide a measure of elastic and rigidity in the cornea 114 of the subject.

As seen from FIG. 1, the illumination system comprises a THz generator head including the femtosecond laser 122 and a nonlinear optical crystal (i.e., the THz transmitter 112). The optical system is arranged in an optical path of the THz illumination system to relay and focus oblique-angle illumination of terahertz radiation on the subject's eye 114 at the focal point 124. The illumination optical system, which can be open space or fiber connected, includes a pair of off-axis parabolic mirrors 126, 128 and a pick-up optical system configured to provide the return beam of terahertz radiation also includes a pair of off-axis parabolic mirrors 130, 132. The detection system 116 is configured to detect said return beam of terahertz radiation within a frequency band of about 0.1 THz to about 10 THz.

The system 100 for dry eye analysis measures the cornea as well as the ambient tissues thickness and the chemical component extraction at individual layers of the eye. The THz radiation measuring system 100 incorporates a small robust femtosecond laser head (the femtosecond laser 122) and a fast optical delay line 134 enabling a sampling signal at or larger than 150 Hz per second (i.e., 6-7 milliseconds). Using systems and methods in accordance with the present embodiments, patients can be scanned without even noticing the scanning.

Figure 2:
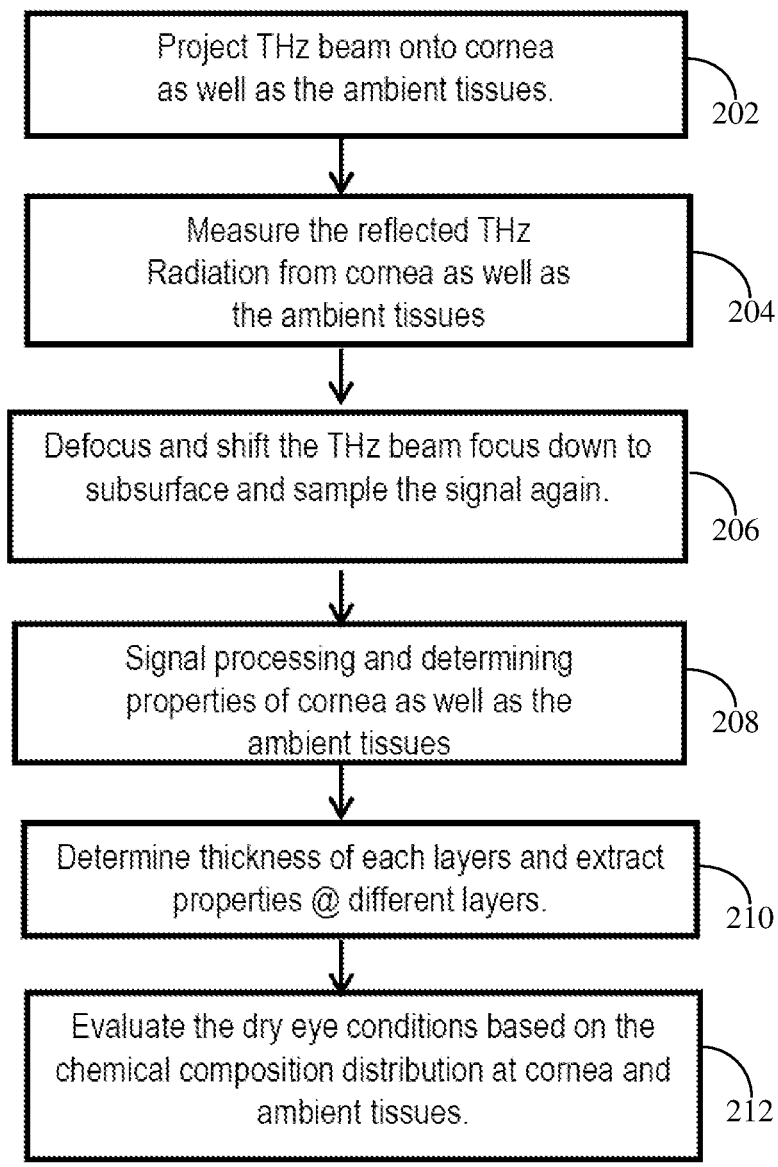
FIG. 2 depicts a flowchart of a method for dry eye analysis in accordance with the present embodiments using the terahertz radiation measuring system of FIG. 1.

FIG. 2 depicts a flowchart 300 of an exemplary method for dry eye analysis in accordance with the present embodiments. The method includes projecting THz radiation onto the eye's cornea as well as ambient tissues of the eye 202. The reflected THz signal reflected from the cornea and/or the ambient tissues of the eye and arriving at the detector 116 is measured 204. Then, the beam of terahertz radiation 110 is defocused and refocused to a subsurface/sublayer of the cornea and/or ambient tissue and measured a second time 206. The signal processing unit 120 processes the terahertz radiation signal 118 to determine 208 properties of the cornea and/or the ambient tissues of the eye. The thickness of layers and the properties (e.g., amount of chemical components) of the layers are determined 210 by the computer 104. Finally, the dry eye conditions are evaluated 212 based on the chemical composition distribution in the cornea and in the ambient tissues of the eye.

Figure 3:
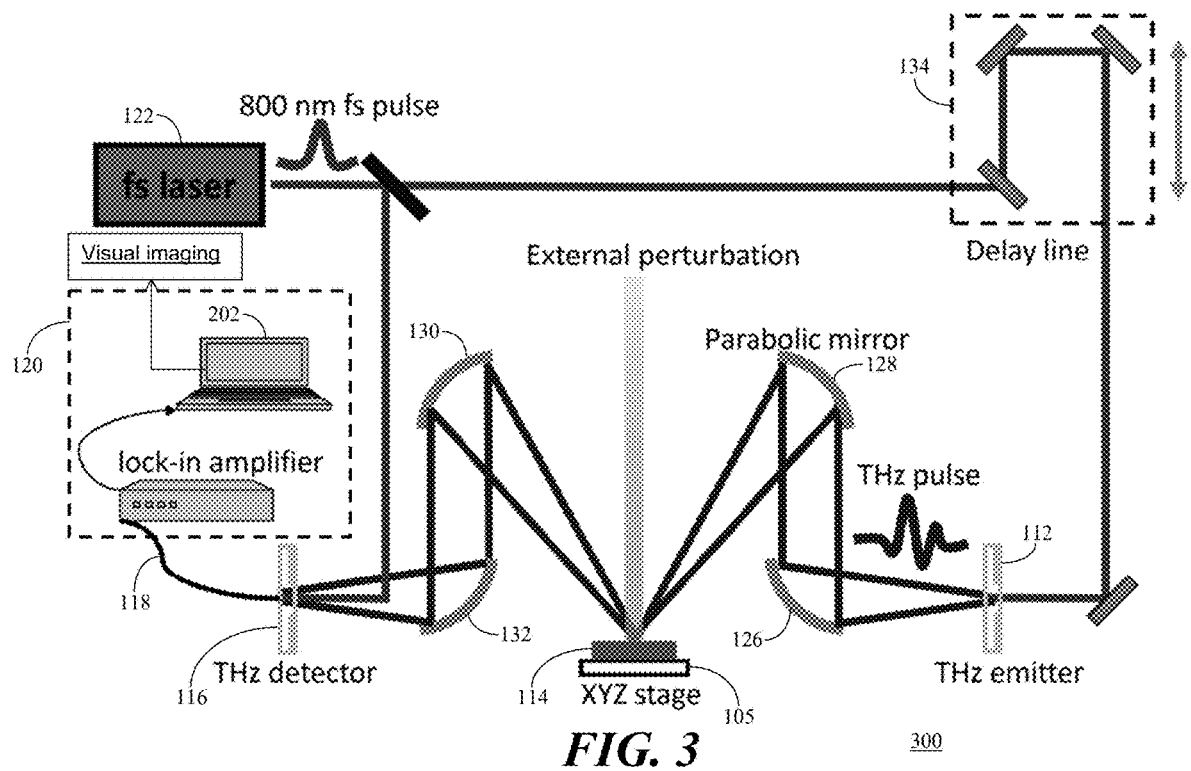
FIG. 3 depicts an illustration of a system for dry eye analysis in accordance with the present embodiments using the terahertz radiation measuring system of FIG. 1.

One of objectives of the present embodiments is to provide a non-contact, in vivo. non-invasive system for analyzing and evaluating dry eye conditions of an eye. Referring to FIG. 3, an illustration 300 depicts use of the system 100 for performing dry eye analysis of a subject's eye 114 in accordance with the present embodiments. To achieve the above objective, the present embodiments provide a non-invasive system for measuring properties of the subject's eye 114 including measuring the thickness of the cornea and/or the ambient tissues and/or measuring an amount of chemical components of one or more of the eye's layers. The terahertz radiation measuring system (THz-TDS) includes the THz wave generator 112 and the THz detector 116 and generates terahertz radiation before and after defocusing and refocusing to measure cornea and ambient tissue properties. The signal processing unit 120 includes a computer 202 which controls the terahertz radiation measuring system (THz-TDS), as well as analysing properties of the eye in response to the THz wave reflected from the surface of the eye. The computer 202 includes a user friendly interface to control the THz source and detection, to analyse the data and do the necessary corrections and display the results and graphs In accordance with the present embodiments, the chemical components of the eye's layers for analyzing dry eye include chemical components such as collagen, hydration and keratocytes. The computer 202 analyses the properties of the eye by determining the properties of one or more layers of the eye, such as calculating a relative corneal composition of the chemical components in the eye's cornea or determine an absolute corneal composition of the chemical components at positions of different cornea layer interfaces using a predefined calibration method, where the different cornea layer interfaces include an interface between the eye's cornea and a layer selected from an epithelium layer, a stromal layer, and an endothelium layer. The absolute corneal composition of the chemical components may include a point value that is an absolute corneal hydration for at least one local region of the eye's cornea. Furthermore, the computer 202 may calculate an overall average of one or both of the thickness or the chemical components of the eye's cornea in response to the THz wave reflected from the surface of the eye using a predetermined model. Thus, the system 300 is able to differentiate the cornea layers (epithelium, epithelium/stromal interface, stromal as well as stromal/endothelium interface) and extract the components (hydration, collagen, keratocytes) in terms of layer.

The THz band represents a unique combination of relatively high spatial resolution with the low scatter and large interaction with chemical bonding at the molecular level. Thus, THz radiation has become a powerful tool for assessing chemical molecular materials. THz spectroscopy can identify an amount absorption fingerprint of the cornea and ambient tissue chemical components (e.g., collagen and keratocytes) by monitoring fingerprint peak positions, intensities and phase changes, which can be correlated to physical structure changes related to dry eye.

The present embodiments use a THz pulse to detect eye ambient tissues chemical components, different cornea layers and interfaces. Through fast fourier transform (FFT) analysis of frequency domain spectra, absorption peaks of water, collagen and keratocytes can be identified. Chemical components of the cornea at individual layers as well as of ambient tissues can be extracted. While a conventional cornea hydration sensing has been reported, it is unrelated to dry eye analysis and such sensing could only detect surface hydration level without other chemical components analysis and did not disclose any analysis of individual interfaces or different layers of the cornea and also did not disclose any analysis of layer thickness.

The present embodiments are technologically significant in the way that they allow extraction of cornea as well as ambient tissue chemical component information in accordance with different layers instantly (i.e., in milliseconds), non-invasively, and non-destructively without the patient sensing the measurements being performed.

Figure 4:
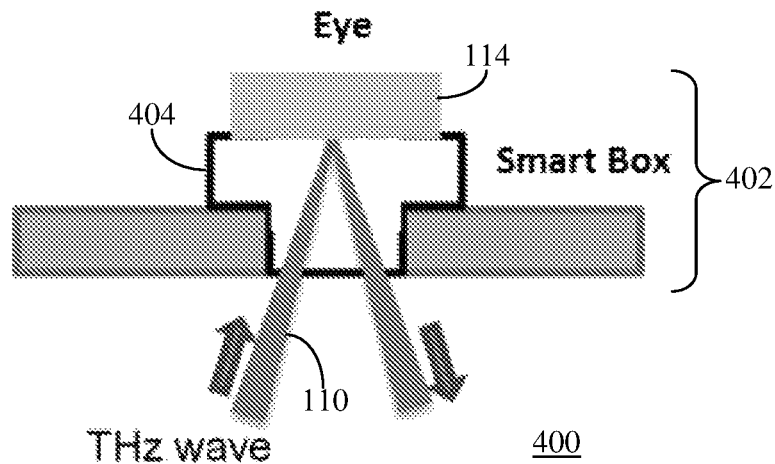
FIG. 4 depicts a planar cross-sectional view of a smart box interface for use with the system of FIG. 3 to enhance sensitivity and/or selectivity of dry eye analysis of an eye in accordance with the present embodiments.

Referring to FIG. 4, a planar cross-sectional view 400 depicts a smart box interface 402 for use with the system 300 to enhance sensitivity and/or selectivity of dry eye analysis of an eye 114 in accordance with present embodiments. The XYZ stage 105 is configured to hold the THz structure, scan the eye 114 and move the THz focus point 124 to different places/layers of the eye 114. To enhance the sensitivity and selectivity of the collagen and keratocyte detection signals in the THz range, a smart box 404 can be inserted between the beam of THz radiation 110 and the eye 114. The smart box 404 can also offset hydration effects from the environment by using hydration absorption materials or low refractive index materials such as polyethylene.

The computer 202 communicates with THz-TDS measuring system 100 and can be configured to process the generated signal 118. The computer 202 may be further configured to create a visual image of the THz response. The XYZ stage 105 can be coupled to the computer 202 to move THz focal point 124 to scan the eye 114 and scan different layers of the eye 114.

Due to the presence of water in physiological tissue and the high THz absorption of water, reflective THz imaging has distinct advantages over transmission-based systems, especially for in vivo applications. The dielectric properties of water absorption frequencies yield easily detectable changes in THz reflectivity. Small changes in hydration levels demonstrate an effective contrast mechanism in THz spectral. These advantages coupled with the low, non-ionizing THz photon energy (i.e., 0.4-40 meV) makes THz radiation an ideal tool for in vivo imaging of skin burns, melanoma/carcinoma, corneal pathologies, and cancers as well as for in vivo dry eye analysis.

Figure 5:
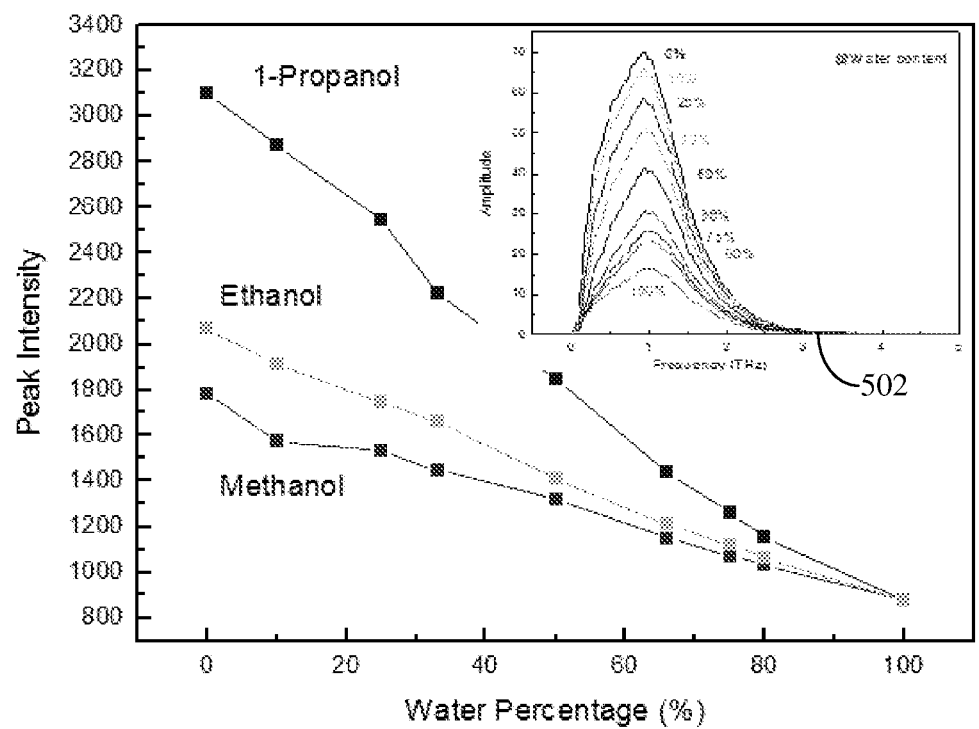
FIG. 5 depicts a graph of terahertz radiation signals of hydroxide bonds and free liquid water at different concentrations as measured by the system of FIG. 3 in accordance with the present embodiments.

Referring to FIG. 5, a graph 500 depicts terahertz radiation signals of hydroxide bonds and free liquid water at different concentrations as measured by the system 300 in accordance with the present embodiments. Hydration-sensitive data and imagery in many test targets is a mixture of chemical and liquid water. Table 1 identifies the chemicals propanol, ethanol and methanol and the graph 500 depicts deionized water mixed with these chemicals at different concentrations.

TABLE 1

| Compound | IUPAC Name | Common Name |
| --- | --- | --- |
| $CH_3OH$ | Methanol | Methyl alcohol |
| $CH_3CH_2OH$ | Ethanol | Ethyl alcohol |
| $CH_3CH_2CH_2OH$ | 1-Propanol | Propyl alcohol |

Both THz peak intensities and peak positions show good correlation with the water concentration. The in-set graph 502 shows the frequency domain spectral where the peaks indicate water absorption. As water mixing with collagen and keratocytes with different concentrations will also show trendy spectral, water concentrations in the cornea and the ambient tissues of the eye can be calculated. By comparing the measured samples with standard samples, a method is prescribed to extract absolute hydration, collagen and keratocytes concentration levels. In addition, ex vivo corneas such as porcine corneas, in a variety of configurations and hydration states can be used to define the relationship between corneal hydration and terahertz reflectivity.

Figure 6:
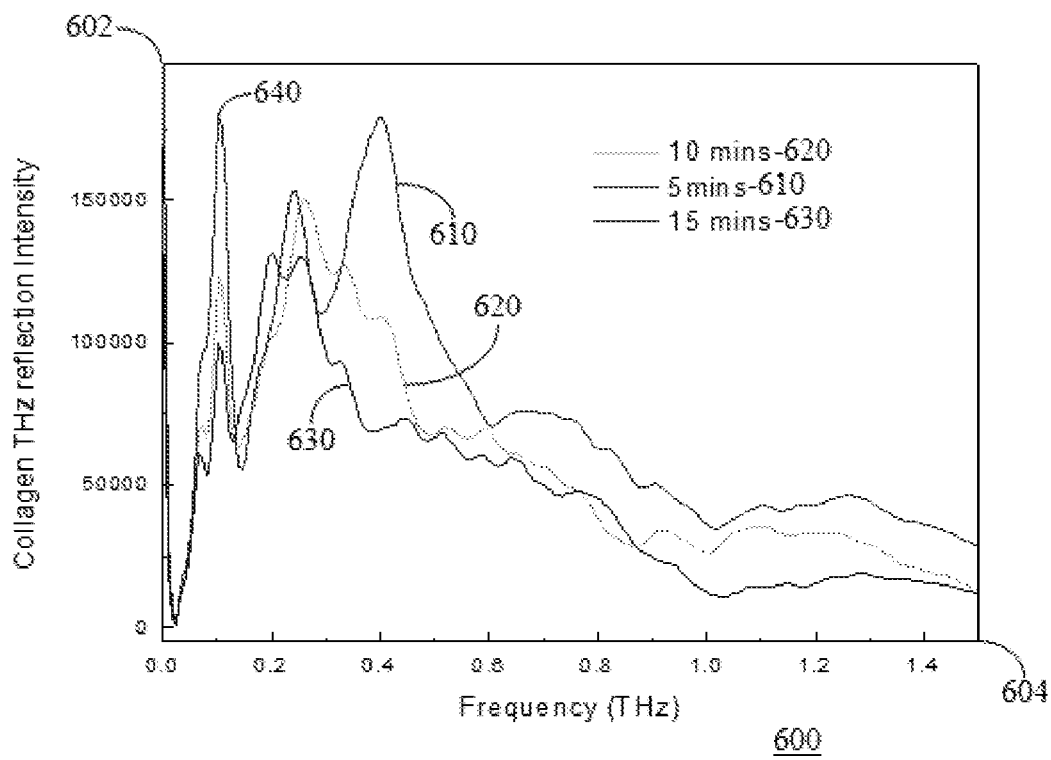
FIG. 6 depicts a graph of monitoring of cultured collagen samples by terahertz radiation signals using the system of FIG. 3 in accordance with the present embodiments.

Referring to FIG. 6, a graph 600 depicts monitoring of cultured collagen samples by terahertz radiation signals using the system 300 in accordance with the present embodiments. A series of pure cultured collagen sheets were tested using the THz-TDS system 300. The intensity 602 vs. frequency 604 is graphed for the cultured collagen samples at five minutes 610, ten minutes 620 and fifteen minutes 630. The obvious observation is that the peak 640 at 0.065 THz is stable. This collagen peak 640 is discernible in THz radiation measurement of chemical components in the cornea and/or ambient tissues of the eye.

Figure 7:
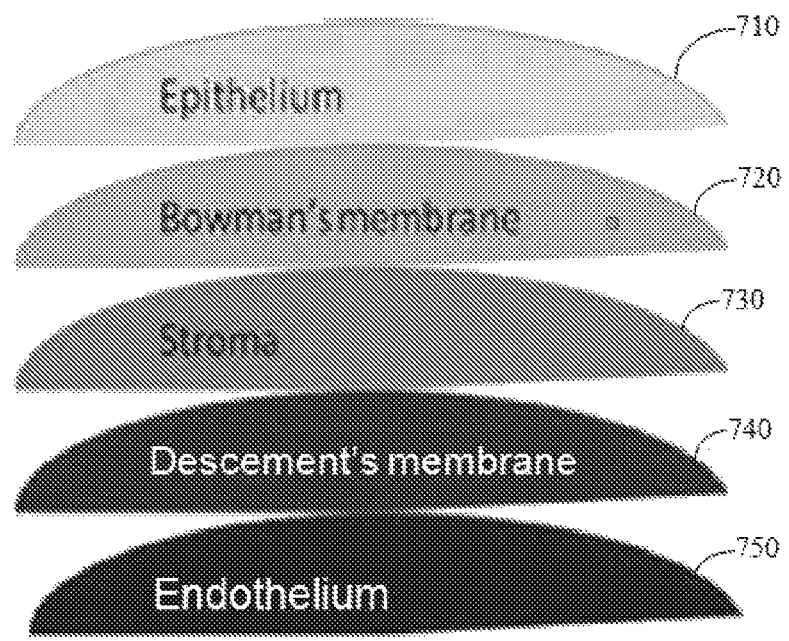
FIG. 7 depicts an illustration of layers and layer interfaces of the cornea of an eye.

Referring to FIG. 7, an illustration 700 depicts layers and layer interfaces of the cornea of an eye. Epithelial tissues line the outer surfaces of organs and blood vessels. The epithelium 710 is the outer surface of the cornea of the eye. An interface, the Bowman's membrane 720, separates the epithelium 710 from the stroma 730. The Descement's membrane 740 is an interface between the stroma 730 and the endothelium 750.

In order to determine the interference between surfaces, layers and interfaces when measuring properties of the layers with THz radiation, the epithelium and stroma layers of porcine eyes were investigated. Referring to FIGS. 8A and 8B, illustrations 800, 820 depict focusing the terahertz radiation 110 through the epithelial layer 802 and into the stroma layer 804 of the eye (the illustration 800) and focusing the terahertz radiation 110 through the stroma surface 810 and into the stroma layer 804 of the eye where the epithelial layer 802 has been stripped off the stroma layer 804 (the illustration 820). Referring to FIGS. 8C and 8D, the graphs 840, 860 illustrate how sublayer properties can be extracted non-invasively by focusing terahertz radiation through the epithelial layer and into the stroma layer of the eye. The graph 840 depicts the THz-TDS spectra collected from reflection of the terahertz radiation 110 focusing of the illustration 800 and the graph 860 depicts the THz-TDS spectra collected from reflection of the terahertz radiation 110 focusing of the illustration 820. It can be seen that with and without the epithelium layer 802, the 0.2 to 0.4 THz peak 842, 862 in the deep in focus 844, 864 and the 0.2 to 0.4 THz peak 846, 866 in the stromal surface focus 848, 868 in both graphs 840, 860 shows the same peak position and intensity for the stromal information. This shows that by focusing the THz radiation 110 through surface with the epithelium 802 intact, the stromal layer 804 chemical component information can be directly detected. The 0.067 THz peaks 850, 870 are from collagen components in the stromal layer 804. The peak positions 850, 870 remain unchanged with or without the epithelial layer 802. The collagen peaks 850, 870 can thus be used as to analyze the corneal health as well as used as an indicator to extract other information such as indirectly extract corneal hydration level.

Figure 9A:
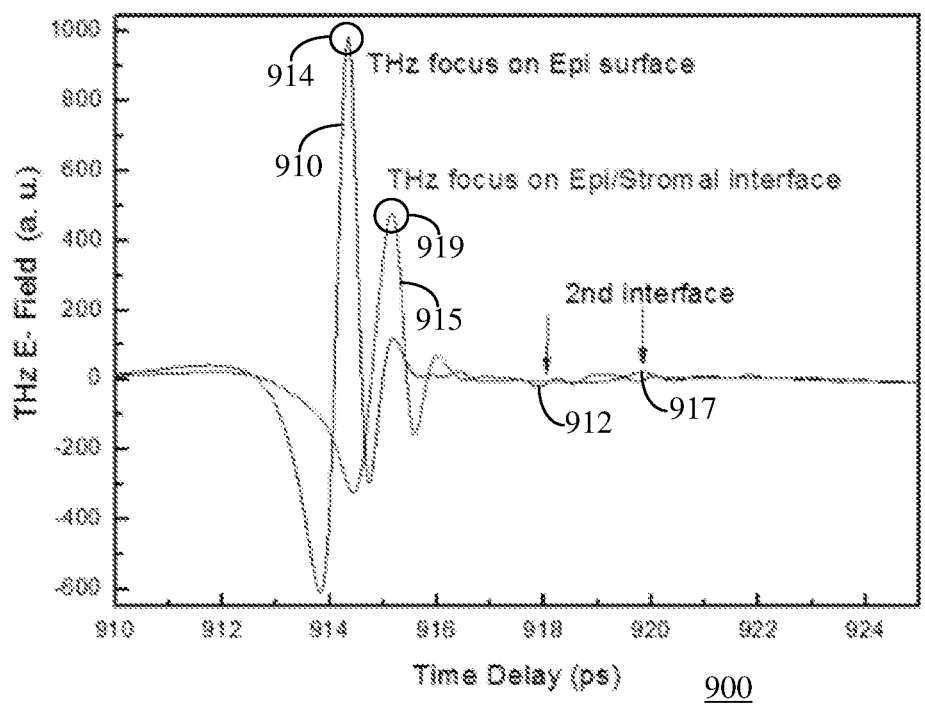
Figure 9B:
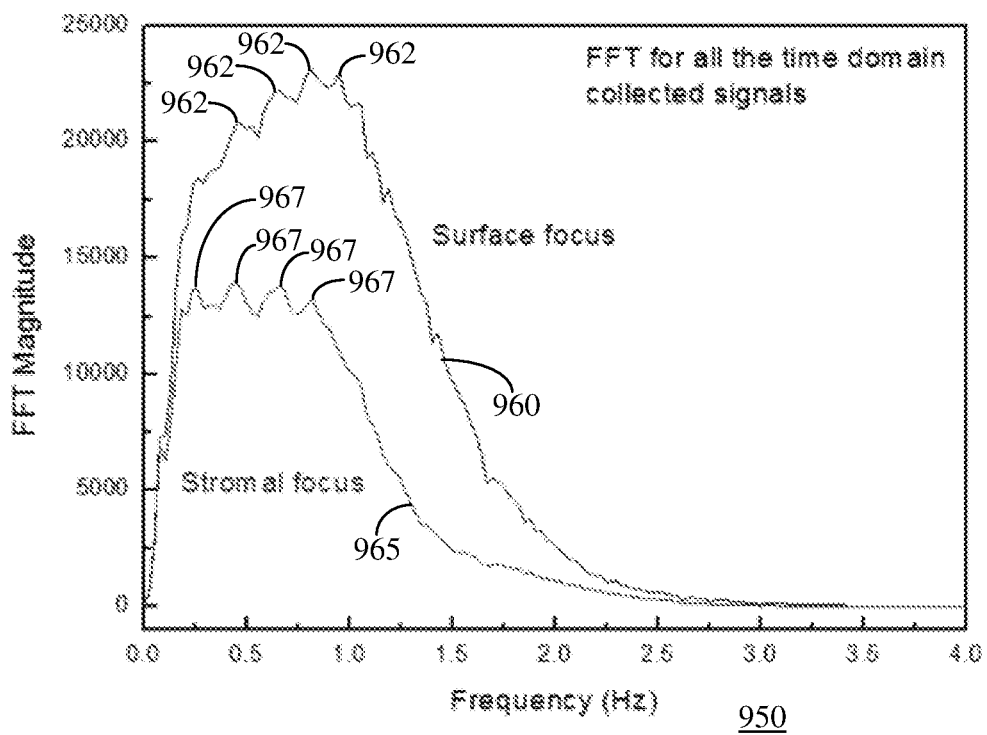

In order to successfully observe the fingerprint of the cornea, the samples were covered using a simple paperbox and, while the THz curves show decreased air-water vapour effects, the time domain and frequency domain signals show much smoother curves. FIGS. 9A and 9B depict graphs 900, 950 of properties of an epithelial layer of the eye as terahertz radiation is focused through the epithelial layer in accordance with the present embodiments using the system 300. The graph 900 depicts a time domain spectra 910 of the THz radiation focused on the epithelium surface and a time domain spectra 915 of the THz radiation focused on the epithelium-stroma interface. The graph 950 depicts a frequency domain spectra 960 of the THz radiation focused on the epithelium surface and a frequency domain spectra 965 of the THz radiation focused on the epithelium-stroma interface. As the terahertz radiation beam is focused from the epithelium surface down through the epithelium to the epithelium stroma interface, the time domain spectra shifted from 910 to 915. The second peaks shifted from 912 to 917 which indicate a second interface. The epithelium/stromal interface and the stromal quality is crucial information input for successful operation rate and minimized post-surgery complications for LASIK correction surgery as the anterior stromal is the site cut during LASIK.

From the graph 950, in the frequency domain when focused on the surface and epithelium/stromal interface, some character peaks 962, 967 can clearly be identified. However, these peaks are likely water vapour absorption peaks and collagen/keratocytes fingerprint peaks.

Figure 10A:
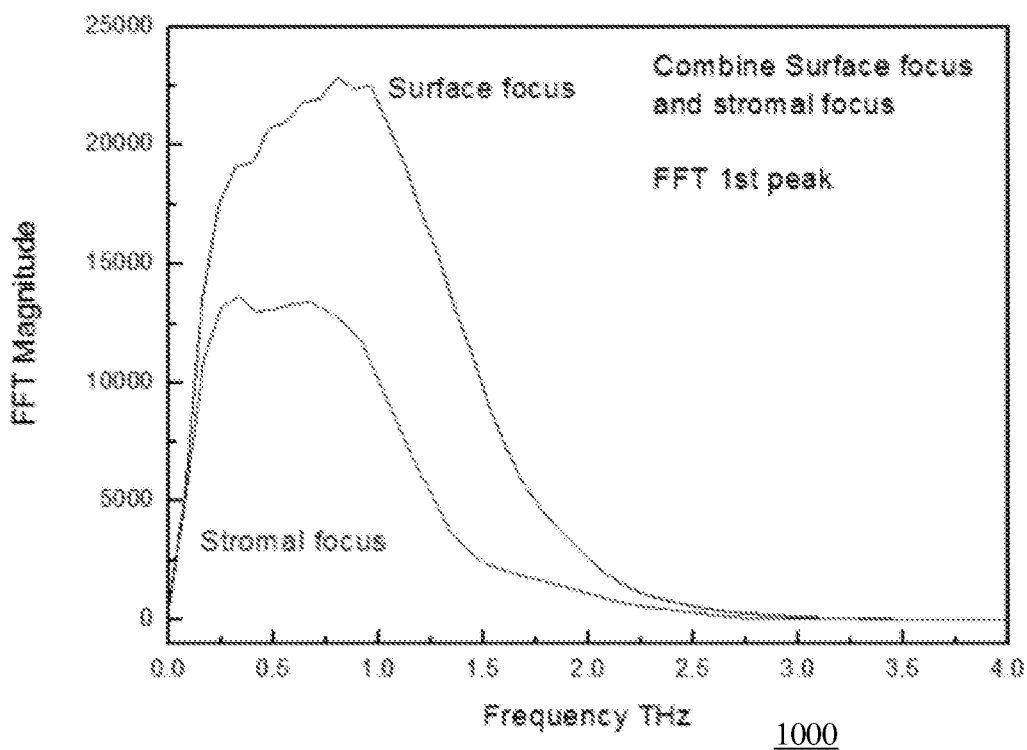
Figure 10B:
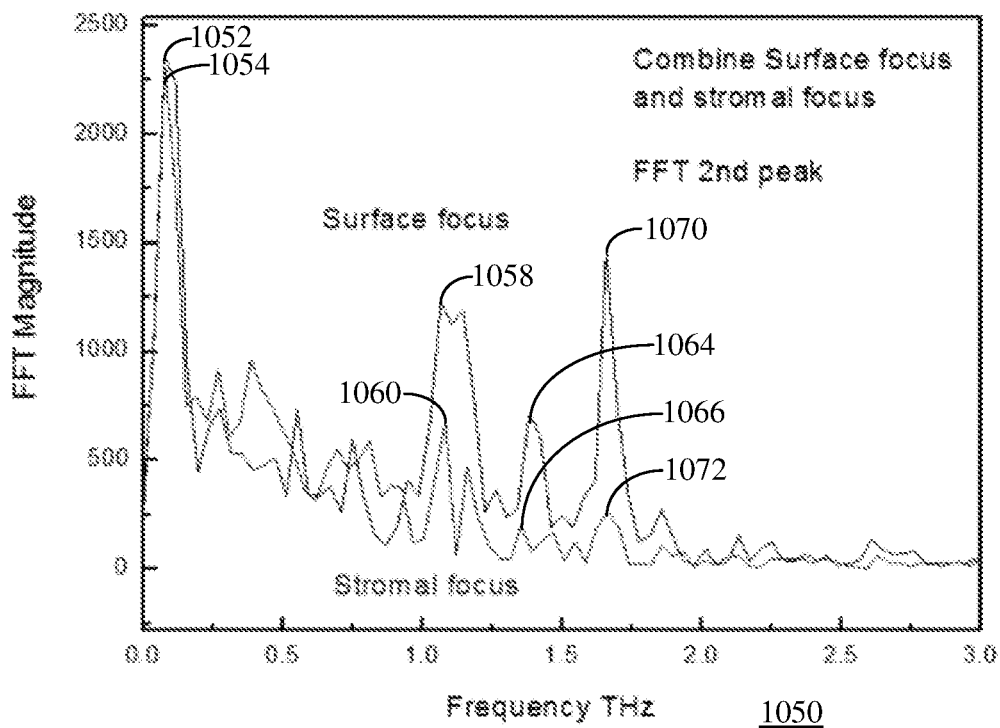

In order to identify each layers' information, two main peaks 914, 919 which represent the epithelium surface and epithelium/stromal interface are identified in the time domain graph 900. Fast Fourier transform (FFT) is performed separately in order to observe the frequency domain characteristic peaks separately. FIGS. 10A and 10B depict graphs 1000, 1050 of frequency domain characteristics of the epithelial layer of the eye in accordance with the present embodiments as derived from the frequency domain spectra of the graph 950. The graph 1000 depicts the frequency domain spectra 960 when FFT is performed on data only for the first peak 914 (FIG. 9A) and the graph 1050 depicts the frequency domain spectra 965 when FFT is performed on data only for the second peak 919 (FIG. 9A). Obvious fingerprint peaks 1052, 1054 can be identified at 86 GHz, peaks 1058, 1060 at 1.1 THz, peaks 1064, 1066 at 1.4 THz, and peaks 1070, 1072 at 1.65 THz can be easily identified. From these results, the epithelium layer hydration level and components can be separately analysed. The stromal layer hydration level, collagen and keratocytes distribution can also be analysed directly.

Figure 11:
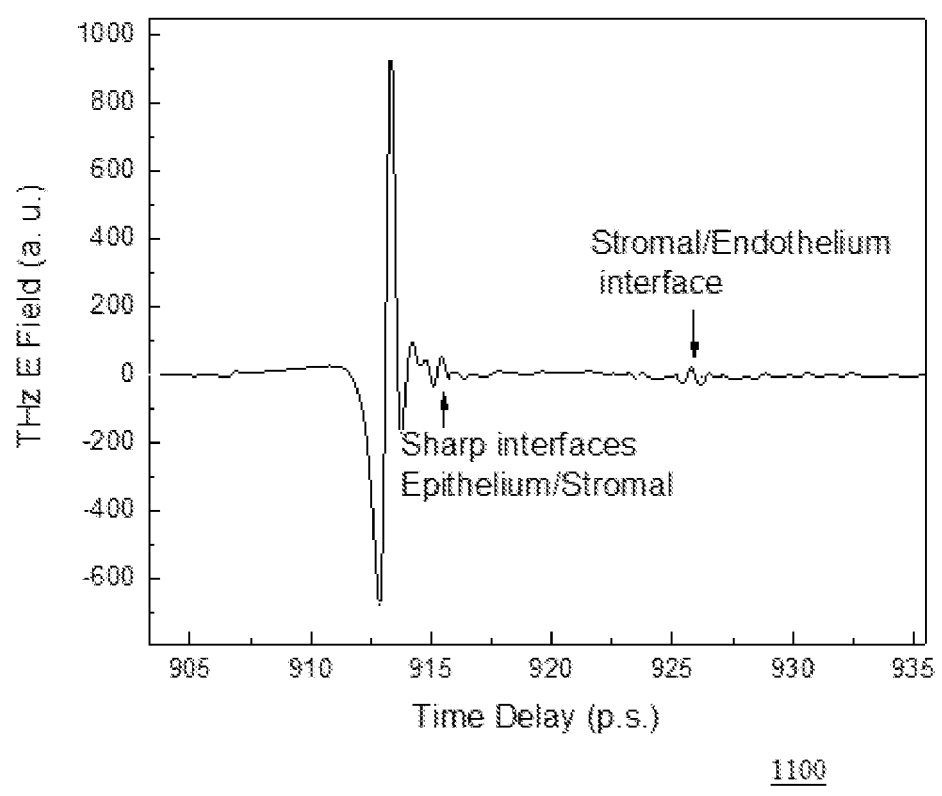
FIG. 11 depicts a graph of time domain spectra for corneal layer thickness measurement by the system of FIG. 3 in accordance with the present embodiments.

Another objective of the present embodiments is to provide a rapid and non-contact method to measure corneal thickness. To achieve this objective, the systems and methods in accordance with the present embodiments utilize the reflected terahertz signals from a front surface of a cornea and a rear interface of the cornea to determine the corneal thickness. The amount of reflection from the rear surface of the cornea is small compared with the amount of reflection from the front surface of the cornea. When reflected terahertz radiation is received by the detector 116 (FIG. 3), the peak of the reflected THz from the rear surface is smaller than that from the front surface of the cornea. The cornea thickness is then related to the time delay of the two signals and the refractive index of the cornea. The greater the time delay is, the thicker the cornea layer is. Furthermore, the each individual layers of the corneal can be extracted from the time of flight between peaks of sub interfaces. FIG. 11 depicts a graph 1100 of time domain spectra for corneal layer thickness measurement by the system of 300 in accordance with the present embodiments. The time of flight between the $2^{nd}$ and $3^{rd}$ peaks is correlated to the thickness of the stromal layer. The precise thickness can be corrected further based on the optical parameters derived.

Figure 12A:
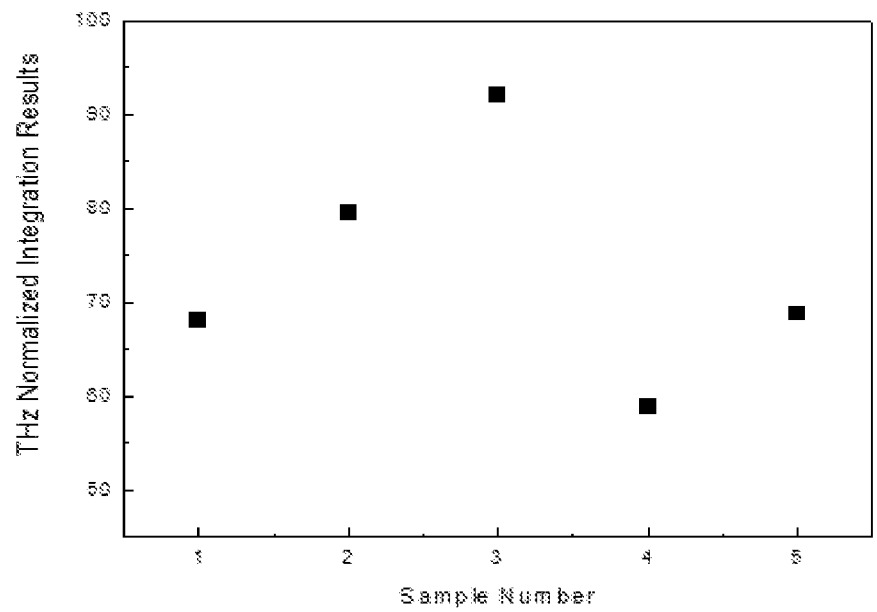
Figure 12B:
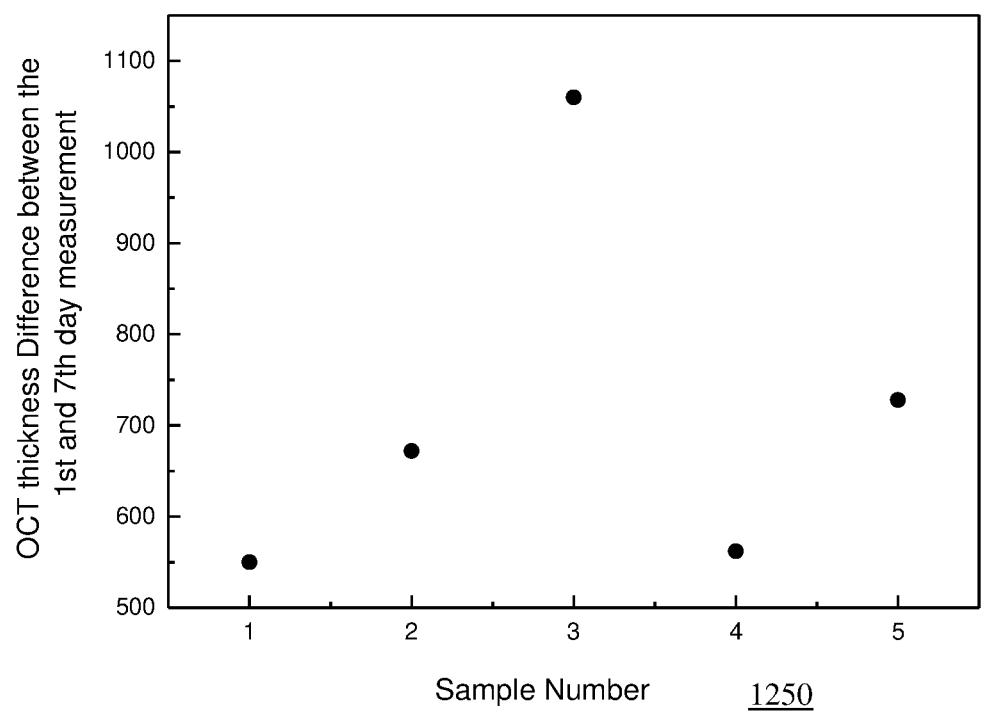

FIGS. 12A and 12B depict graphs 1200, 1250 comparing time domain spectra results using terahertz radiation in accordance with the present embodiments of a set of five porcine eyes with ocular corneal thickness (OCT) measurements using conventional systems of the set of five porcine eyes. The graph 1200 depicts a time domain spectra results using terahertz radiation in accordance with the present embodiments and the graph 1250 depicts the OCT measurements using conventional systems. It can be seen that the THz spectra results has almost the same trend as the OCT results. The OCT results are acknowledged to be a proximal reflection of the corneal hydration level. However, the OCT suffers serious deviation from the real hydration level of the cornea. The THz spectra advantageously provides a more precise and more reliable value of corneal hydration level as compared with the OCT results. Yet, the similar trends given out by THz TDS in the graph 1200 and the OCT in the graph 1250 prove that THz radiation in the systems and methods in accordance with the present embodiments can identify the properties of the eye.

The present embodiments are technologically significant in the way that they allow extraction of cornea as well as ambient tissue chemical component information in accordance with different layers instantly (i.e., in milliseconds), non-invasively, and non-destructively without the patient sensing the measurements being performed. Thus, it can be seen that the present embodiments provide rapid in vivo non-invasive systems and methods for dry eye analysis. The non-destructive and non-contact systems and methods in accordance with the present embodiments evaluate corneal and ambient tissue layer thickness changes and chemical components changes within individual layers of a subject's eye with enhanced sensitivity and selectivity for dry eye tissue analysis.

While exemplary embodiments have been presented in the foregoing detailed description of the invention, it should be appreciated that a vast number of variations exist. It should further be appreciated that the exemplary embodiments are only examples, and are not intended to limit the scope, applicability, operation, or configuration of the invention in any way. Rather, the foregoing detailed description will provide those skilled in the art with a convenient road map for implementing an exemplary embodiment of the invention, it being understood that various changes may be made in the function and arrangement of steps and method of operation described in the exemplary embodiment without departing from the scope of the invention as set forth in the appended claims.

What is claimed is:

1. A system for dry eye analysis using terahertz (THz) radiation, the system comprising:
   a terahertz radiation measuring system comprising:
      a terahertz radiation generator configured to project a THz wave onto a surface of an eye, the terahertz radiation generator comprising an optical delay line configured to provide a sampling rate of the THz wave of at least 150 Hz;
      a stage configured to focus the THz wave to the surface of the eye or a layer below the surface of the eye; and
      a terahertz radiation detector configured to detect a reflected wave being a reflection of the THz wave reflected from the surface of the eye or a layer below the surface of the eye;

a smart box interface between the THz wave and the eye, the smart box interface comprising a smart box comprising low refractive index material and/or hydration absorption material for enhancement of sensitivity or selectivity of analysis of properties of the one or more layers of the eye; and a signal processing unit comprising a computing device, the signal processing unit configured to communicate with the terahertz radiation detector to analyse the properties of one or more layers of the eye in response to the THz wave reflected from the surface of the eye or a layer below the surface of the eye, the properties of the one or more layers of the eye comprising a thickness of the eye's cornea and ambient tissues and an amount of a plurality of chemical components in the one or more layers of the eye, wherein the signal processing unit is further configured to extract the analyzed properties of the one or more layers of the eye;

wherein the computing device of the signal processing unit is configured to process a signal representing the reflected wave to determine the thickness of the cornea and the thickness of the ambient tissues of the one or more layers of the eye and the amount of the plurality of chemical components of the one or more layers of the eye to generate an evaluation of the dry eye conditions of the eye, and to present results of the evaluation of the dry eye conditions of the eye and visual imaging of the analyzed properties of the cornea or the one or more layers of the eye.

2. The system in accordance with claim 1 wherein the chemical components of the eye's layers comprise a chemical component selected from collagen, hydration and keratocytes.

3. The system in accordance with claim 1 wherein the computing device is configured to calculate a relative corneal composition of the chemical components in the eye's cornea.

4. The system in accordance with claim 1 wherein computing device is configured to determine an absolute corneal composition of the chemical components at positions of different cornea layer interfaces using a predefined calibration method, and wherein the different cornea layer interfaces comprise an interface between the eye's cornea and a layer selected from an epithelium layer, a stromal layer, and an endothelium layer.

5. The system in accordance with claim 4 wherein the computing device is further configured to calculate a point value that is an absolute corneal hydration for at least one local region of the eye's cornea.

6. The system in accordance with claim 1 wherein the computing device is configured to calculate an overall average of one or both of the thickness or the chemical components of the eye's cornea in response to the THz wave reflected from the surface of the eye or a layer below the surface of the eye using a predetermined model.

7. The system in accordance with claim 1 wherein the terahertz radiation measuring system further comprises an illumination optical system coupled to the terahertz radiation generator to provide oblique-angle terahertz radiation illumination of the surface of the eye and coupled to the terahertz radiation detector to provide the reflected wave thereto, and wherein the illumination optical system comprises optical components connected by open space or optical fiber.

8. The system in accordance claim 7 wherein the illumination optical system comprises two off-axis parabolic (OAP) mirrors, wherein a first mirror of the two OAP mirrors is arranged in an optical path of the terahertz radiation generator and is configured to receive the THz wave emitted from the terahertz radiation generator and reflect at least a portion of the THz wave and project the at least a portion of the THz wave onto the surface of the eye; and wherein a second mirror of the two OAP mirrors is arranged in a symmetrical position to the first mirror with respect to the eye and is configured to receive at least a portion of the THz wave reflected from the eye.

9. The system in accordance with claim 1 wherein the terahertz radiation detector is configured to detect the reflected wave within a frequency band of 0.1 THz to about 10 THz.

10. The system in accordance with claim 1 wherein the terahertz radiation generator further comprises:

a femtosecond laser configured to generate the THz wave; and a terahertz radiation signal emitter configured to emit the THz wave onto the surface of the eye, wherein the terahertz radiation signal emitter is an antenna or a nonlinear crystal.

11. The system in accordance with claim 1 wherein the computing device comprises a user interface configured to display the visual imaging of the analyzed properties of the cornea or the one or more layers of the eye.

12. The system in accordance with claim 11 wherein the computing device is further coupled to the terahertz radiation measuring system, and wherein the user interface is further configured to enable control of the terahertz radiation measuring system.

13. A method for dry eye analysis using terahertz (THz) radiation, the method comprising:

projecting a THz wave onto a surface of an eye such that a sampling rate of the THz wave is at least 150 Hz;

focusing the THz wave to the surface of the eye or a layer below the surface of the eye;

detecting a reflected wave being a reflection of the THz wave reflected from the surface of the eye or a layer below the surface of the eye as a result of projecting the THz wave onto the surface of the eye; and determining properties of one or more layers of the eye in response to the THz wave reflected from the surface of the eye or a layer below the surface of the eye, the properties of the one or more layers of the eye comprising a thickness of the eye's cornea and ambient tissues and an amount of a plurality of chemical components in the one or more layers of the eye;

extracting the properties of the one or more layers of the eye;

analyzing the extracted properties of the one or more layers of the eye to generate an evaluation of the dry eye conditions of the eye; and presenting the evaluation of the dry eye conditions of the eye and visual imaging of the analyzed properties of the cornea or the one or more layers of the eye, wherein projecting the THz wave onto the surface of the eye comprises disposing a smart box interface between the THz wave and the eye, the smart box interface comprising a smart box comprising low refractive index material and/or hydration absorption material for enhancement of sensitivity or selectivity of analysis of the properties of the one or more layers of the eye.

14. The method in accordance with claim 13 wherein the chemical components of the eye's layers comprise a chemical component selected from collagen, hydration and keratocytes.

15. The method in accordance with claim 13 wherein determining the properties of the one or more layers of the eye comprises calculating a relative corneal composition of the chemical components in the cornea of the eye.

16. The method in accordance with claim 13 wherein determining the properties of the one or more layers of the eye comprises determining an absolute corneal composition of the chemical components at positions of different cornea layer interfaces using a predefined calibration method, wherein the different cornea layer interfaces comprise an interface between the eye's cornea and a layer selected from an epithelium layer, a stromal layer, and an endothelium layer.

17. The method in accordance with claim 16 wherein determining the absolute corneal composition of the chemical components comprises calculating a point value that is an absolute corneal hydration for at least one local region of the eye's cornea.

18. The method in accordance with claim 17 wherein determining the absolute corneal composition of the chemical components comprises calculating an overall average of one or both of the thickness or the chemical components of the eye's cornea in response to the THz wave reflected from the surface of the eye or a layer below the surface of the eye using a predetermined model.

\* \* \* \* \*